United States Patent [19]

Cooper et al.

[11] Patent Number: 5,128,882
[45] Date of Patent: Jul. 7, 1992

[54] DEVICE FOR MEASURING REFLECTANCE AND FLUORESCENCE OF IN-SITU SOIL

[75] Inventors: Stafford S. Cooper; Philip G. Malone, both of Vicksburg, Miss.

[73] Assignee: The United States of America as represented by the Secretary of the Army, Washington, D.C.

[21] Appl. No.: 570,679

[22] Filed: Aug. 22, 1990

[51] Int. Cl.$^5$ .................. G06F 15/74; G01N 21/00
[52] U.S. Cl. ................... 364/550; 73/863.23; 364/420; 364/498
[58] Field of Search ............. 364/420, 421, 422, 550, 364/496–499, 555, 525, 526, 527; 250/253, 255, 256; 73/863.23, 151

[56] References Cited

U.S. PATENT DOCUMENTS

| | | | |
|---|---|---|---|
| 4,330,207 | 5/1982 | Nogami et al. | 364/498 |
| 4,446,370 | 5/1984 | Gergely | 364/420 |
| 4,510,573 | 4/1985 | Boyce et al. | 364/498 |
| 4,514,822 | 4/1985 | Schneider et al. | 364/498 |
| 4,573,354 | 3/1986 | Voorhees et al. | 364/420 |
| 4,660,151 | 4/1987 | Chipman et al. | 364/498 |
| 4,674,880 | 6/1987 | Seki | 364/498 |
| 4,914,944 | 4/1990 | Herron et al. | 364/22 |
| 5,010,776 | 4/1991 | Lucero et al. | 73/863.23 |

Primary Examiner—Kevin J. Teska
Attorney, Agent, or Firm—Darrell E. Hollis

[57] ABSTRACT

A method and apparatus for real time, on-site detection and analysis of contaminant in soil, the invention continuously measures and records specific spectral properties of potentially contaminated soil along a typically vertical profile as a soil penetrating probe of the invention penetrates the soil. The probe is fitted with a light transparent window and a light source disposed internally of the probe. Light from internally of the probe passes through the window and is reflected back through the window from the soil as the probe passes through the soil, the light reflected from the soil back through the window being collected by a fiber optic link within the probe. The collected light is then transmitted through the fiber optic link to the surface for measurement and recordation of spectral distribution and intensity. Determination of the type and amount of contaminant is possible by comparison of the spectral signature of the soil to standards prepared by adding known concentrations of specific contaminant to soil similar to the soil found on the test site. The invention thus allows rapid on-site determination of the location, depth and quantity of contaminant in soils and particularly soils in waste disposal sites.

21 Claims, 2 Drawing Sheets

DEVICE FOR MEASURING REFLECTANCE AND FLUORESCENCE OF IN-SITU SOIL

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

1. Field of the Invention

The invention relates generally to detection and analysis of contaminant in soil and particularly to a method and apparatus for on-site determination of the type, location and quantity of contaminant in soils by measurement of the spectral signature of the soils.

2. Description of the Prior Art

Soil contamination studies must periodically be conducted at hazardous waste sites and are also conducted in other situations where soil contamination is suspected. Such studies have typically involved the use of a soil auger to dig a hole to a desired depth for sampling. A tube sampler is then pushed or hammered into the bottom of the auger hole to obtain the sample which must then be extracted from the sampler, packed for shipping and then sent to a suitable laboratory facility for characterization of any contaminants present in the soil sample. The auger is then used once again after extraction of the first sample to clean out and deepen the sampling hole with the entire sampling process then being repeated. This prior art procedure is notoriously slow, and does not produce a continuous record of contaminant distribution in the soil. As is apparent, this prior art process only produces an intermittent record of contaminant distribution and further requires a very substantial amount of time not only to take the samples but to put together an analysis of the samples. Further, due to the possibility of contaminants being present in the soil being tested, the auger cuttings require special handling. The tube samplers must also be cleaned after each use so as not to contaminate subsequent samples. Analysis of the samples requires a substantial amount of time and delay due to the necessity for laboratory work. Field sampling must often be repeated in the prior art process when laboratory analyses prove faulty or if errors in sampling occur. The prior art has not previously provided the ability to produce a continuous record of contaminant distribution in soil and certainly has not provided the ability to produce such a continuous record in real time and on site. The present invention provides such capability and further produces no waste material which must be disposed of and does not expose test personnel on site to samples of contaminated soil. The invention further eliminates the requirement for the packing and shipping of soil samples to a laboratory for analysis along with the resultant delays. Since soil contamination can be immediately detected during testing, test personnel can effect changes in the testing procedure as necessitated by the data being collected in real time.

SUMMARY OF THE INVENTION

The invention provides method and apparatus for detection and analysis of contaminant in soil by measuring variations in specific spectral properties such as fluorescence or visible/ultraviolet absorbance as a soil probe passes through the soil being tested. Practice of the invention allows rapid, real time determination of the type, location, depth and quantity of contaminant in soils while on the site which is being testing. According to the invention, light is passed from internally of a test probe into the soil through which the probe is passing, light reflected from the soil is collected and transmitted through a fiber optic link to instrumentation The collected light is then analyzed to determine spectral distribution and intensity, the resulting spectral signature being compared to standards prepared by adding known concentrations of specific contaminants to soil similar to the soil found on the site being tested. Variations in specific spectral properties are thus measured and calibration curves are constructed which relate to concentration of a specific contaminant in soil to a particular spectral characteristic. Rapid, real time and on-site analysis is thus possible, the analysis providing an indication of the type of contaminant, the location and depth of the contaminant and the quantity of the contaminant which is present in the soil.

A soil penetrating probe configured according to the invention is formed of a pointed, hollow metal body which is capable of penetrating most soils to a depth of 100 feet or more. This soil penetrating probe is fitted with a light transparent window on one side and with a light source disposed internally of the probe. Light from the light source passes through the window in the probe and irradiates soil passing past the window as the probe is advanced into the soil. Light reflected back through the window from the irradiated soil is collected by a fiber optic link disposed within the probe, the link transmitting the collected light to the surface for measurement and recordation of spectral distribution and intensity. On the surface, the collected light is received by a spectral analysis unit which may comprise a spectrophotometer, filter colorimeter or an optical multi-channel analyzer for determination of the intensity of the light as a function of wavelength. The spectral information is shown on a display unit and archived in a data storage unit with a printer/plotter being used to produce a hard copy of the spectral information for on-site review. A real time plot of the spectral characteristics of the soil as the probe advances through the soil is thus produced and is immediately available to test personnel. Changes in the spectral signature of the soil which is indicative of contamination can be used to determine the depth and concentration of a specific contaminant or contaminants. Such information can be immediately used to identify testing steps to be either immediately undertaken or undertaken at a later time.

Use of the technology represented by the present method and apparatus provides a number of practical advantages which reduce risk to test personnel and which provide savings in both temporal and financial resources. In particular, as compared to methodology used in the prior art as referred to hereinabove, use of the present technology produces no potentially contaminated quantities of soil which must be disposed of and further does not expose test personnel to samples of contaminated soil. The present technology also permits a substantially greater number of testing procedures to be conducted over a given period of time than is possible with prior art testing methodology. Among a number of other advantages, use of the present technology provides immediate information useful in guiding further and future sampling of soils and also indicates preferred location for direct placement of ground-water monitoring wells and the like so that safety protocols can be developed which influence additional investigations and remedial actions.

Accordingly, it is an object of the invention to provide a method and apparatus for rapid and real time on-site detection and analysis of contaminant in soil through continuous measurement and recordation of specific spectral properties of potentially contaminated soil.

It is another object of the invention to provide a method and apparatus capable of producing a continuous record of contaminant distribution in soil through measurement of reflectance, fluorescence or absorbance characteristics of the soil.

It is a further object of the invention to provide a method and apparatus for on-site analysis of contaminant in soil wherein the apparatus comprises a soil penetrating probe having an internal light source and a light transparent window formed in the probe and wherein light is directed from internally of the probe through the window and reflected from the soil passing past the window and back into the probe through the window for collection by a fiber optic link within the probe, the spectral signature of the soil passing past the window providing an indication of the type, location, depth and quantity of contaminant in the soil.

Further objects and advantages of the invention will be more readily apparent in light of the following detailed description of the invention.

DESCRIPTION OF THE PREFERRED EMBODIMENTS

Figure 1:
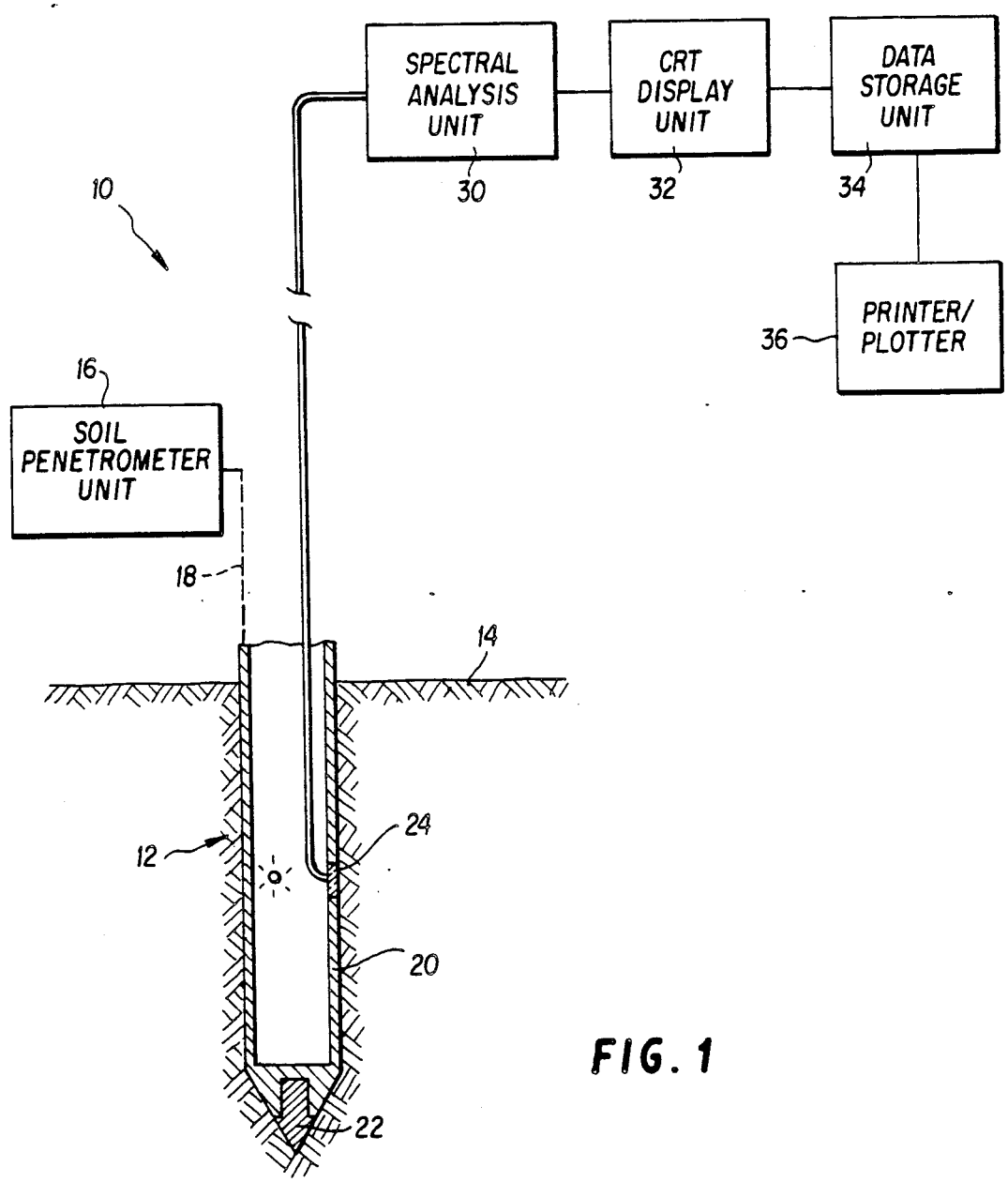
FIG. 1 is a schematic of the contaminant detection and analysis system of the invention.

Referring now to the drawings and particularly to FIG. 1, the detection and analysis system of the invention is seen generally at 10 to comprise a penetrometer probe shown generally at 12. The penetrometer probe 12 comprises that portion of the system 10 which penetrates soil 14 and which is driven downwardly through the soil to a desired depth. It should be understood that the probe 12 is configured to transmit information continuously back to the surface as the probe 12 is driven into the soil.

Apparatus capable of "pushing" the probe 12 into the soil 14 is shown generally at 16 and is generally identified as a soil penetrometer unit which includes a drive rod 18 shown schematically in FIG. 1. The soil penetrometer unit 16 and rod 18 are of conventional construction and are known in the art. Typically, the rod 18 is of a diameter which is substantially equal to or slightly less than the diameter of the probe 12, the rod diameter typically being approximately 1.4 inches. Through use of the drive rod 18, the soil penetrometer unit 16 is capable of causing penetration of the probe 12 through most soils to a depth of at least 100 feet. The soil penetrometer unit 16 causes advance of the probe 12 through the soil at a rate of approximately 2 cm per second. The penetration of the probe 12 through the soil can be stopped at any point if additional time is required for study of information being transmitted back to the surface. Since the structure of the soil penetrometer unit 16 and of the drive rod 18 is conventional, no further description will be provided in order that the particular advances of the present invention may be more fully addressed.

Continuing to refer to FIG. 1, the penetrometer probe 12 is seen to comprise a housing 20 which is substantially cylindrical in conformation and which terminates at its distal end in tip 22, the tip 22 being tapered to a point and functioning to facilitate penetration of the soil 14. Details of the structure of the penetrometer probe 12 will be described hereinafter relative to FIGS. 2 and 3.

Figures 2, 3:
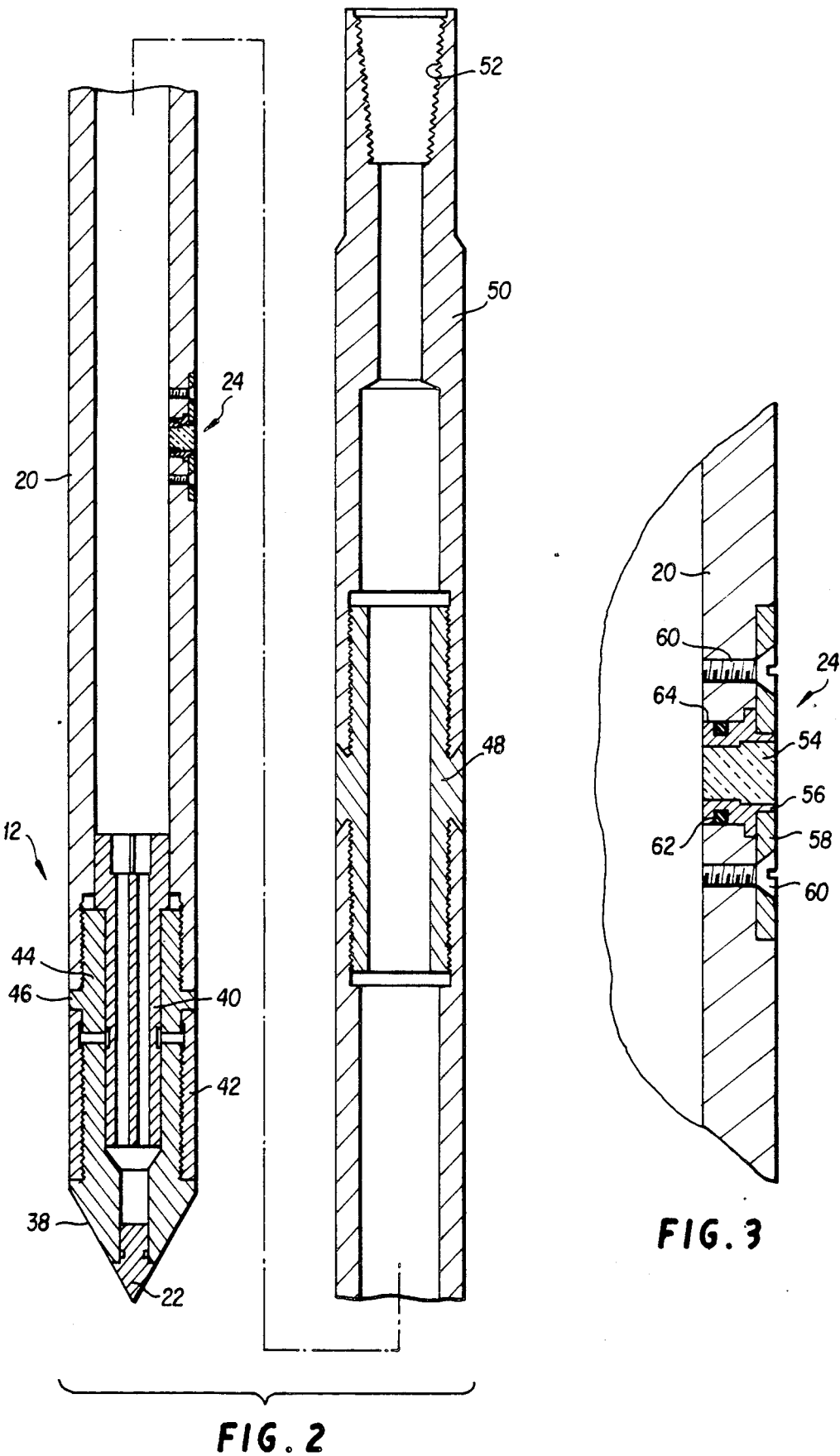
FIG. 2 is an elevational view in section illustrating the soil penetrating probe of the invention; and, FIG. 3 is a detail elevational view in section of the light transparent window formed in the soil penetrating probe.

As will be realized from a review of the details of the structure of the probe 12 in FIGS. 2 and 3, the probe 12 is represented in an idealized fashion in FIG. 1 for ease of illustration. A transparent window 24 is seen to be fi&ted into a wall of the housing 20. A light source 26 or plurality of light sources are disposed within the interior of the penetrometer probe 12 at a location which allows light to pass through the transparent window 24 and irradiate that soil which is immediately outside of the window 24 as the probe 12 passes through the soil. The irradiated soil reflects or transmits light back through the window 24 where the reflected light is collected by a fiber optic link 28. The fiber optic link 28 transmits this reflected light to instrumentation on the surface. The collected light is first passed from the link 28 to a spectral analysis unit 30 which can comprise a spectrophotometer filter colorimeter or optical multi-channel analyzer. The spectral analysis unit 30 determines light intensity as a function of wavelength and passes the spectral information to a CRT display unit 32 which allows test personnel to immediately glean certain information from the system 10. The information displayed by the unit 32 can further be passed to data storage unit 34 and a hard copy can be produced on site by means of a printer/plotter 36 which is connected to the data storage unit 34.

Complete analysis of the spectral information produced by the system 10 is provided by a comparison of the spectral information with standards prepared by mixing known quantities of contaminants with soil similar to that found on the proposed test site. Variations in specific spectral properties, such as fluorescence or visible or ultraviolet absorbance, are measured and calibration curves are constructed which relate the concentration of a specific contaminant in soil to particular spectral characteristics. The preparation of such calibration curves is within ordinary skill in the art and need not be described in detail herein. The system 10 thus provides a spectral signature which allows determination of the type and amount of contaminant by comparing the spectral signature of the soil 14 at a particular time to the aforesaid standards which are prepared by adding known concentrations of specific contaminants to soil similar to that found on the test site. The system 10 thus rapidly determines the type, location, depth and quantity of contaminant on the site. The real time, on-site analysis provided by the system 10 allows much faster and safer analysis than is possible with conventional soil surveys which require drilling, sampling and off-site analysis. Further, the system 10 provides both temporal and financial savings in soil investigations at waste disposal sites and otherwise.

The penetrometer of probe 12 can be configured in a variety of ways without departing from the scope of the invention. For example, the light source 26 can take the form of a filament lamp, a gas discharge lamp or a light-emitting diode mounted within the hollow housing 20 and can be powered by an external power source or by a battery carried within the housing 20. Light source 26 could also take the form of a lamp or laser located on the surface and coupled with the fiber optic link 28 or with another link to transmit light from the surface to the transparent window 24. If light is to be transmitted from the surface, a single fiber optic link can be used to transmit light pulses from the surface and to return the reflected and/or fluorescence energy to the surface for analysis.

The fiber optic link 28 can be formed from a silica or quartz fiber, or fiber bundle, that is capable of transmitting the radiation of interest to the surface. If a single fiber is to be used to transmit light from a light source at the surface and to collect reflective and/or fluorescent energy, the fiber must be efficient at transmitting both types of radiation.

The transparent window 24 must be fabricated of a durable material which is transparent to radiation which must pass through the window from the light source 26 and which is reflected or fluoresced back through the window 24 from the soil. A suitable material which is transparent both to ultraviolet and visible light and which has the required durability is sapphire.

Considering now the surface instrumentation used in the system 10, a spectrophotometer filter colorimeter or optical multi-channel analyzer can provide the spectral analysis required as the unit 30. A real time display of the spectral characteristics of the soil can be output to a liquid crystal display or to a plasma display rather than the cathode ray tube display unit 32 which is explicitly shown and described above. Data storage such as is provided by the unit 34 can be accomplished through the use of any electromagnetic media, optical discs, etc.

The system 10 shown in FIG. 1 is thus see to provide a real time plot of the spectral characteristics of the soil as the probe 12 is advanced down into the soil 14. The system 10 rapidly provides a continuous record of contaminant distribution in the soil without the necessity for off-site analysis of soil samples.

Referring now to FIGS. 2 and 3, particular details of the structure of the penetrometer probe 12 can be appreciated. The probe 12 as noted above is comprised of the housing 20 with the tip 22. In order to maintain structural integrity as the probe 12 is being driven into the soil, the probe 12 is configured in a manner which is best seen in FIG. 2. At the opposite end of the housing 20 is a sealing adaptor 48 which separates this end of the housing from a pipe sub 50. The pipe sub 50 is provided with joints 52 which allow attachment of the drive rod 18 (not shown in FIG. 2) so that the probe 12 can be pushed into the soil by means of the soil penetrometer unit 16 as described above.

Referring now to FIG. 3, a detail view of the transparent window 24 can be seen to be comprised of a sapphire window element 54 which extends between the interior and exterior of the housing 20. The window element 54 is held in place by means of a mounting cell 56 and a flat retainer plate 58, the plate 58 being held to the housing 20 by means of flat head screws 60. An O-ring 62 seals the mounting cell from oppositely disposed surfaces of bore 64 formed in the housing 20. Before fitting of the window element 54, mounting cell 56, retaining plate 58 and screws 60 in place, the side of the probe is milled flat along with surrounding portions of the housing 20 in order to prevent burrs and obstructions extending from the window 24 and surrounding area which would prevent soil from moving smoothly over the window 245 as the probe 12 moves through the soil.

FIGS. 1 and 2 show the light source 26 and fiber optic link 28 of FIG. 1.

Although the invention has been described explicitly relative to particular embodiments thereof, it is to be understood that the invention can be practiced other than as described herein, the definition of the invention being limited only by the scope of the appended claims.

What is claimed is:

1. Apparatus for producing on-site and in real time a continuous record of contaminant distribution in soil, comprising:
   a. a probe for penetrating the soil;
   b. means for driving the probe into the soil;
   c. a window formed in the probe for allowing transmission of light between the exterior and interior of the probe;
   d. light means disposed internally of the probe for producing light in the range from visible through ultra violet which passes through the window to irradiate the soil adjacent the window as the probe passes through the soil;
   e. light collection and transmission means disposed internally of the probe for collecting reflected light or fluorescence passing back through the window from the soil; and,
   f. analysis means receiving the reflected light or florescence from the light collection and transmission means for analyzing said reflected light or fluorescence to produce a spectral signature for each locus of the soil through which the probe passes, said spectral signatures containing information on the contaminants present in the soil.

2. The apparatus of claim 1 wherein the probe comprises a hollow body having a pointed tip which facilitates penetration of the probe into the soil.

3. The apparatus of claim 2 wherein the light means comprise a light source disposed internally of the probe means.

4. The apparatus of claim 3 wherein the window comprises a light transparent element formed of sapphire and means fitted into a wall of the hollow body for mounting the light transparent element, the light transparent element allowing the passage of light between the interior and exterior of the hollow body.

5. The apparatus of claim 4 wherein the light collection and transmission means comprise a fiber optic link which receives light entering the hollow body through the transparent window element and transmitting that light to the analysis means.

6. The apparatus of claim 5 wherein the analysis means comprises a spectral analysis unit comprised of an optical multi-channel analyzer.

7. The apparatus of claim 5 wherein the analysis means comprises a spectral analysis unit comprised of a spectrophotometer.

8. The apparatus of claim 7 wherein the analysis means further comprises means for displaying spectral signatures of the soil analyzed by the spectral analysis unit.

9. The apparatus of claim 7 wherein the analysis means further comprises means for comparing the spectral signature of the soil passing by the transparent window element with predetermined spectral characteristics of similar soils having known quantities of contaminant admixed therewith.

10. The apparatus of claim 9 wherein the analysis means further comprises means for storing data produced by the spectral analysis unit.

11. The apparatus of claim 1 wherein the light collection and transmission means comprise a fiber optic link which receives light entering the probe means through the window means and transmitting that light to the analysis means.

12. The apparatus of claim 11 wherein the analysis means comprises a spectral analysis unit comprised of a spectrophotometer filter colorimeter.

13. The apparatus of claim 11 wherein the analysis means comprises a spectral analysis unit comprised of an optical multi-channel analyzer.

14. The apparatus of claim 12 wherein the analysis means further comprises means for displaying the spectral signatures of the soil analyzed by the spectral analysis unit.

15. The apparatus of claim 12 wherein the analysis means further comprises means for comparing the spectral signature of the soil passing by the window means with predetermined spectral characteristics of similar soils having known quantities of contaminant admixed therewith.

16. The apparatus of claim 15 wherein the analysis means further comprises means for storing data produced by the spectral analysis unit.

17. A method for producing on-site and in real time a continuous record of contamination distribution in soil, comprising the steps of:
   a. irradiating a portion of the soil with light in the range from visible to ultra-violet from a source of light as the light source passes through a bore formed in the soil;
   b. collecting the light reflected or fluoresced from the soil as a result of irradiation of the soil;
   c. analyzing the collected reflected or fluoresced light to produce a spectral signature for each locus of the soil irradiated by the light.

18. The method of claim 17 including the further step of comparing the spectral signature thus produced with predetermined spectral characteristics of similar soils having known quantities of contaminant admixed therewith.

19. A method for producing on-site and in real time a continuous record of contamination distribution in soil, comprising the steps of:
   a. penetrating the soil with a probe;
   b. irradiating a portion of the soil from a source of light in the range from visible to ultra-violet disposed internally of the probe adjacent a window in the probe;
   c. collecting and transmitting reflected light or fluorescence passing back through the window from the soil;
   d. analyzing the reflected light or fluorescence to produce a spectral signature for each locus of the soil through which the probe passes.

20. The method of claim 19 including the further step of displaying the spectral signatures of the soil analyzed.

21. The method of claim 19 including the further step of comparing the spectral signature with predetermined spectral characteristics of similar soils having known quantities of contaminant admixed therewith.

* * * * *